United States Patent
Ando et al.

(10) Patent No.: US 9,650,599 B2
(45) Date of Patent: May 16, 2017

(54) APPARATUS FOR CULTURING CELLS AND METHOD FOR CULTURING CELLS

(71) Applicant: Panasonic Intellectual Property Management Co., Ltd., Osaka (JP)

(72) Inventors: Takeshi Ando, Kyoto (JP); Toshinori Hirose, Osaka (JP); Soichiro Fujioka, Osaka (JP); Norihiro Shibata, Osaka (JP); Osamu Mizuno, Nara (JP); Toshiaki Yamauchi, Kyoto (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 0 days.

(21) Appl. No.: 14/762,201

(22) PCT Filed: Dec. 22, 2014

(86) PCT No.: PCT/JP2014/006368
§ 371 (c)(1),
(2) Date: Jul. 20, 2015

(87) PCT Pub. No.: WO2015/098080
PCT Pub. Date: Jul. 2, 2015

(65) Prior Publication Data
US 2015/0353882 A1    Dec. 10, 2015

(30) Foreign Application Priority Data

Dec. 26, 2013 (JP) ................. 2013-268666

(51) Int. Cl.
*A61K 38/08* (2006.01)
*C12M 1/34* (2006.01)
*C12M 3/00* (2006.01)
*C12M 1/00* (2006.01)
*C12M 1/36* (2006.01)

(52) U.S. Cl.
CPC ............ *C12M 41/26* (2013.01); *C12M 23/48* (2013.01); *C12M 29/00* (2013.01); *C12M 41/48* (2013.01)

(58) Field of Classification Search
CPC ...................................... C12M 23/48
See application file for complete search history.

(56) References Cited

U.S. PATENT DOCUMENTS

| | | | |
|---|---|---|---|
| 4,812,392 | A | 3/1989 | Miyake et al. |
| 2003/0194805 | A1 | 10/2003 | Minamigawa et al. |
| 2008/0014637 | A1 | 1/2008 | Minamigawa et al. |

FOREIGN PATENT DOCUMENTS

| | | |
|---|---|---|
| EP | 189599 | 8/1986 |
| JP | 61-152273 | 7/1986 |
| JP | 61-152282 | 7/1986 |
| JP | 2003-009853 | 1/2003 |
| JP | 2007-110932 | 5/2007 |
| WO | 97/31128 | 8/1997 |

OTHER PUBLICATIONS

Webster et al. J. Clin. Invest., 1999, 104:239-252.*
International Search Report of PCT application No. PCT/JP2014/006368 dated Mar. 17, 2015.
The Extended European Search Report dated Feb. 18, 2016 for the related European Patent Application No. 14870654.2.

\* cited by examiner

*Primary Examiner* — Bin Shen
(74) *Attorney, Agent, or Firm* — Panasonic IP Management; Kerry S. Culpepper

(57) ABSTRACT

An apparatus for culturing cells using a culture medium, including: a replacer that replaces the culture medium in a culture vessel held by a holder; a measurer that measures a pH of the culture medium in the culture vessel; and an instructor that instructs the replacer to replace the culture medium in the culture vessel, wherein the instructor gives an instruction when the pH measured by the measurer is less than a predetermined pH threshold at a first replacement of the culture medium, and gives an instruction when the pH measured by the measurer is less than the predetermined pH threshold and the interval is less than an interval of a previous replacement of the culture medium at second and subsequent replacements of the culture medium.

4 Claims, 5 Drawing Sheets

APPARATUS FOR CULTURING CELLS AND METHOD FOR CULTURING CELLS

CROSS-REFERENCE TO RELATED APPLICATIONS

This application is a U.S. national stage application of the PCT International Application No. PCT/JP2014/006368 filed on Dec. 22, 2014, which claims the benefit of foreign priority of Japanese patent application 2013-268666 filed on Dec. 26, 2013, the contents all of which are incorporated herein by reference.

TECHNICAL FIELD

The present invention relates to cell cultivation.

BACKGROUND ART

Generally, culturing cells have been performed using a culture medium. The culture medium is a culture solution containing a large amount of nutritive substances. When the time of using the culture medium is longer, the pH of the culture medium is decreased due to influences such as lactic acid produced by cell growth. When the pH of the culture medium is decreased, the pH is out of a range suitable for cell growth and the cell culture state may become inactive. Among conventional apparatuses for culturing cells, there is an apparatus that replaces a culture medium at regular intervals according to the kind of cell, in order to keep the pH range of the culture medium constant (for example, refer to PTL 1).

The apparatus disclosed in PTL 1 extrapolates the pH of the culture medium from changes in color of phenol red contained in the culture medium, and replaces the culture medium when the extrapolated pH is determined to be unsuitable for cell growth.

FIG. 6 is a diagram showing a relationship between absorbance and pH in the apparatus disclosed in PTL 1. The apparatus disclosed in PTL 1 measures the pH from the absorbance using the relationship shown in FIG. 6 and gives an instruction to replace the culture medium when the measured pH is less than a predetermined value.

CITATION LIST

Patent Literature

PTL 1: Unexamined Japanese Patent Publication No. 61-152282, the contents of which are incorporated herein by reference.

SUMMARY OF THE INVENTION

In regenerative medicine and drug discovery, mass cultivation is simultaneously and parallelly performed using a plurality of culture vessels in some case. In this case, when the timing of replacement of the culture medium is determined using only the pH extrapolated at the time of measurement, culture media in the culture vessels may be needed to be replaced at the same time.

An object of the present invention is to provide an apparatus for culturing cells which is capable of efficiently replacing a culture medium.

In order to achieve the above object, the present invention provides an apparatus for culturing cells using a culture medium, the apparatus comprising: a replacer that replaces the culture medium in a culture vessel held by a holder; a measurer that measures a pH of the culture medium in the culture vessel; and an instructor that gives the replacer an instruction to replace the culture medium in the culture vessel, wherein the instructor gives the instruction when the pH measured by the measurer is less than a predetermined pH threshold at a first replacement of the culture medium, and gives the instruction when the pH measured by the measurer is less than the predetermined pH threshold and an interval is less than an interval of a previous replacement of the culture medium at second and subsequent replacements of the culture medium.

Further, in order to achieve the above object, the present invention provides a method for culturing cells using a culture medium, the method comprising, in order to replace the culture medium in a culture vessel: replacing the culture medium when a pH of the culture medium in the culture vessel is less than a predetermined pH threshold at a first replacement of the culture medium; and replacing the culture medium when the pH of the culture medium in the culture vessel is less than the predetermined pH threshold and an interval is less than an interval of a previous replacement of the culture medium at second and subsequent replacement of the culture medium.

According to the apparatus for culturing cells or the method for culturing cells of the present invention, the replacement of the culture medium can be efficiently performed.

DESCRIPTION OF EMBODIMENT

Hereinafter, the exemplary embodiment of the present invention will be described with reference to the drawings. The same numerals are assigned to the same components, and the description of the components may be omitted. For clear illustration, the drawings are schematically shown mainly on each of the components.

Exemplary Embodiment

Figure 1:
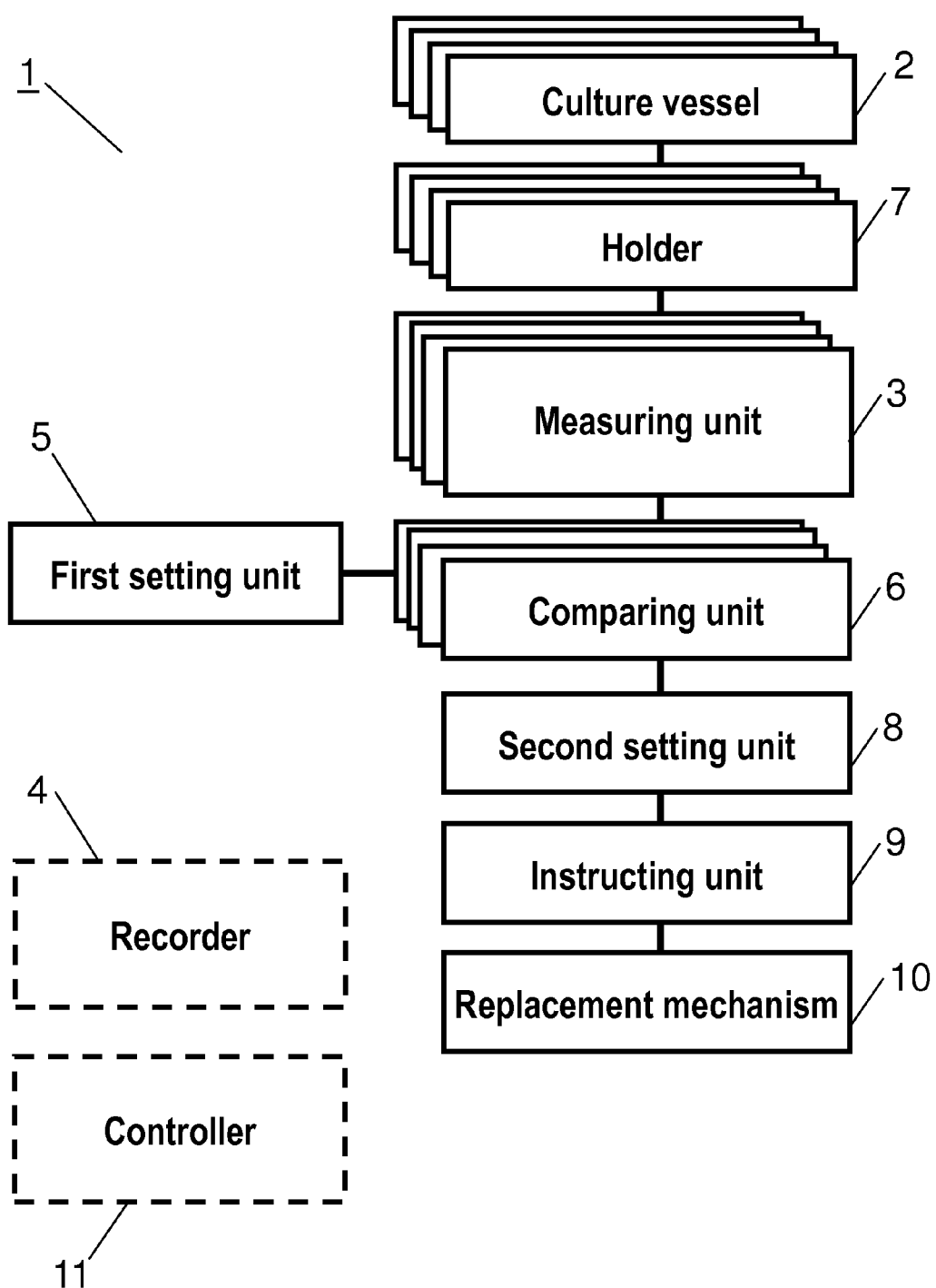
FIG. 1 is a view showing an outline of an apparatus for culturing cells in an exemplary embodiment of the invention.

FIG. 1 is a view showing an outline of apparatus 1 for culturing cells according to an exemplary embodiment of the invention.

Apparatus 1 for culturing cells of the exemplary embodiment is an apparatus that cultivates cells using a culture medium. The method for culturing cells of the exemplary embodiment is a method for culturing cells using apparatus 1 for culturing cells. Here, the term "culture medium" means a culture solution containing a large amount of nutritive substances.

Apparatus 1 for culturing cells comprises a number N (where N is an integer more than or equal to 2) of holders 7, measuring unit 3, recorder 4, first setting unit 5, comparing unit 6, second setting unit 8, instructing unit 9, replacement mechanism 10, and controller 11, as shown in FIG. 1. Here, holders 7 hold one or a plurality of culture vessels 2. Measuring unit 3 is a pH calculating unit, for example. Measuring unit 3 measures the pH of a culture medium in each of culture vessels 2 from the absorbance. Recorder 4 records, for example, the pH which has been measured by measuring unit 3 on time axis, and then records a pH threshold which has been previously set as a threshold by first setting unit 5. First setting unit 5 is a pH setting unit, for example. First setting unit 5 sets a pH threshold for replacing a culture medium. Comparing unit 6 compares the pH threshold set by first setting unit 5 to the pH of the culture medium measured by measuring unit 3. Second setting unit 8 is a culture medium replacement determining unit, for example. Second setting unit 8 reads time changes of pH regarding the culture medium in each of culture vessels 2 in which the pH is below the pH threshold in comparing unit 6 from recorder 4, and determines the priority of the replacement of the culture medium from the read time changes of pH. Instructing unit 9 is a culture medium replacement instructing unit, for example. Instructing unit 9 instructs culture vessel 2 having high priority which has been determined by second setting unit 8 to replace the culture medium. Replacement mechanism 10 is a medium replacing unit, for example. Replacement mechanism 10 replaces the culture medium based on the instruction from instructing unit 9. Controller 11 controls the operation of each configuration of apparatus 1 for culturing cells. Further, the term "the replacement of the culture medium" means replacement of the culture medium in culture vessel 2.

Prior to the explanation of the exemplary embodiment, problems of the conventional apparatus for culturing cells which have been found by the inventor's experiments will be described.

Figure 2:
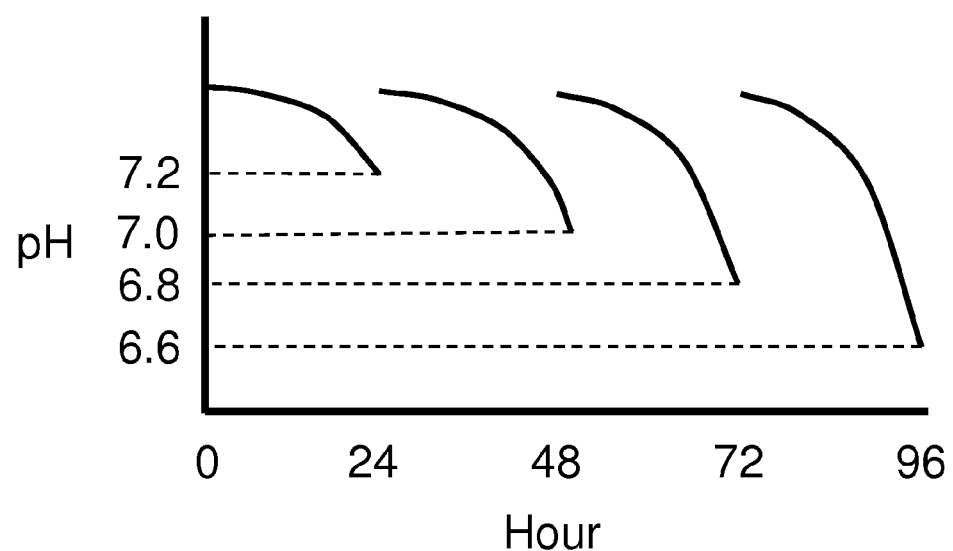
FIG. 2 is a diagram showing a relationship between time and pH in the case where a culture medium is replaced every 24 hours.

Cells seeded in culture vessel 2 undergo cell division over time, which results in an increase in the number of cells. Although the pH of the culture medium decreases over time, the pH of the culture medium can be maintained within a predetermined range by replacing the culture medium every fixed time. In this regard, the number of cells in culture vessel 2 is increased with time. Thus, when the culture medium is replaced at regular intervals, the pH immediately before the replacement of the culture medium is decreased as shown in FIG. 2. FIG. 2 is a diagram showing a relationship between time and pH in the case where the culture medium is replaced every 24 hours, which has been conventionally performed. As shown in FIG. 2, it is found that, in the case where the culture medium is replaced every 24 hours, the pH at the first replacement of the culture medium after 24 hours of cell seeding is 7.2, on the other hand, the pH at the fourth replacement of the culture medium after 96 hours is 6.6. In the case where the pH is 6.6, it may become an unsuitable condition for cell cultivation depending on the kind of cells to be cultivated.

Figure 3:
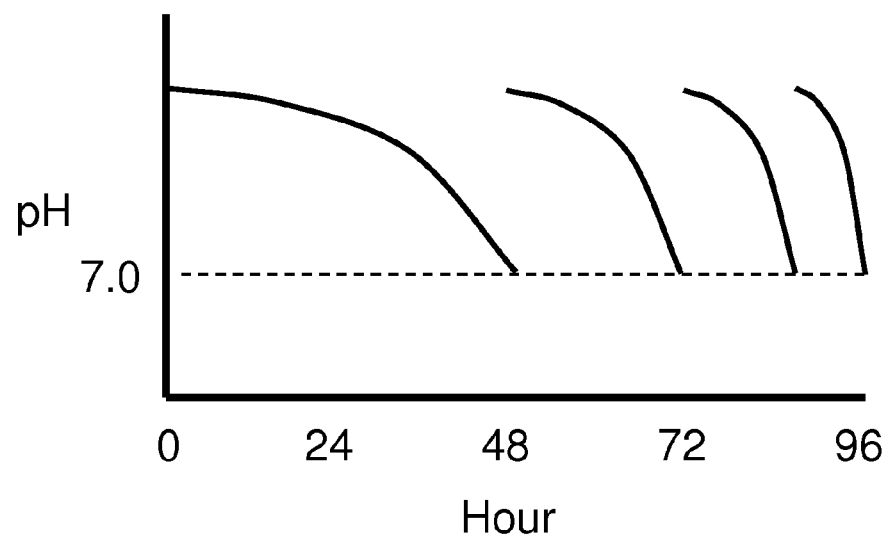
FIG. 3 is a diagram showing a relationship between time and pH in the case where a threshold for replacing a culture medium is pH 7.0 in the exemplary embodiment.
Figure 4:
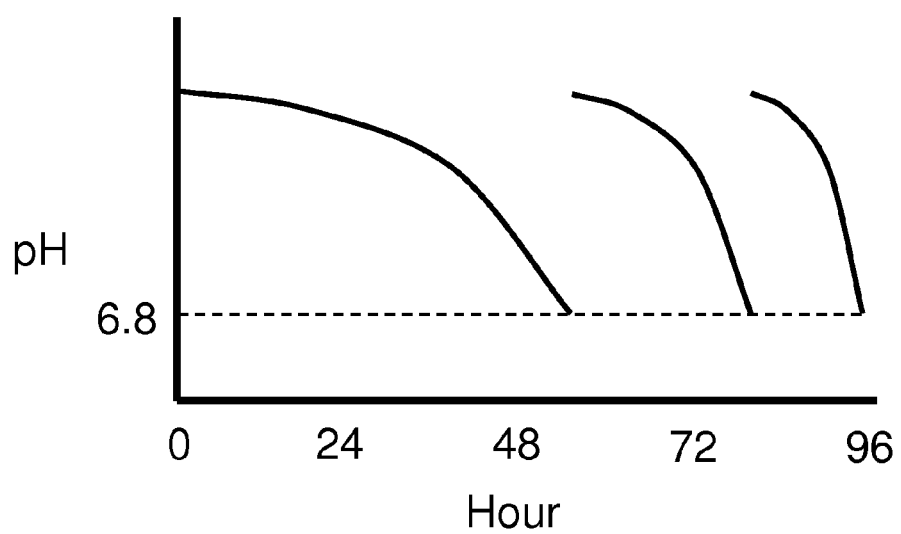
FIG. 4 is a diagram showing a relationship between time and pH in the case where the threshold for replacing a culture medium is pH 6.8 in the exemplary embodiment.

In order to solve the conventional problems, in apparatus 1 for culturing cells of the exemplary embodiment, measuring unit 3 measures the pH of the culture medium in culture vessel 2, compares the measured pH to a pH threshold, and replaces the culture media in the case where the measured pH has a pH below the pH threshold. The experiments by the inventors show that, for example, when the pH threshold for replacing a culture medium is set to a pH of 7.0, the pH changes as shown in FIG. 3. When the pH changes as shown in FIG. 3, the cell cultivation can be carried out in a state where the pH is always 7.0 or more even in the case where the culture medium replacement frequency is the same as that of FIG. 2. Further, the experiments by the inventors show that, for example, when the pH threshold for replacing a culture medium is set to a pH of 6.8, the pH changes as shown in FIG. 4. Through the experiments, the inventors have defined a pH of 6.8 as a pH threshold, i.e., as a lower limit for cell cultivation. It is found that, when the pH changes as shown in FIG. 4, the culture medium replacement frequency can be reduced to once, compared to the case where the culture medium is replaced every 24 hours (shown in FIG. 2). In other words, when the pH threshold for replacing a culture medium is set to 6.8, the consumption of the culture medium can be reduced.

In apparatus 1 for culturing cells of the exemplary embodiment, the timing of the replacement of the culture medium is set to the case where the pH is a predetermined pH threshold and the interval is less than an interval of the previous replacement of the culture medium. According to the experimental results by the inventors as shown in FIGS. 3 and 4, the above configuration allows the cell cultivation to be carried out efficiently in the exemplary embodiment. The term "less than an interval of the previous replacement of the culture medium" means that, for example, in the cell cultivation after performing the replacement of the culture medium twice, an interval between the second replacement of the culture medium and the third replacement of the culture medium is less than an interval between the first replacement of the culture medium and the second replacement of the culture medium. As a matter of course, this condition does not apply to the case where the replacement of the culture medium is never performed. That is, instructing unit 9 of apparatus 1 for culturing cells of the exemplary embodiment gives an instruction to replace the culture medium in the case where the pH measured by measuring unit 3 is less than the predetermined pH threshold at the first replacement of the culture medium, and gives an instruction to replace the culture medium in the case where the pH measured by measuring unit 3 is less than the predetermined pH threshold and the interval is less than the interval of the previous replacement of the culture medium at the second and subsequent replacement of the culture medium.

In the exemplary embodiment, the reason why the term "less than an interval of the previous replacement of the culture medium" is added to the conditions is that, normally, the time the pH reaches a constant pH is shortened with an increase in the number of cells. Note that when the interval of the replacement of the culture medium is not shorter than the interval of the previous replacement of the culture medium, it is extrapolated that the cells being cultured have any abnormality. Therefore, this condition is employed so that the cultivation state can be accurately grasped.

Further, the inventors have examined the replacement of the culture medium in the cell cultivation in the case where a plurality of culture vessels 2 have been used.

When a plurality of culture vessels 2 are used, the timing when the measured pH is below the pH threshold may occur in culture vessels 2 at the same time. In apparatus 1 for culturing cells of the exemplary embodiment, the replacement of the culture medium is performed preferentially in descending order of culture medium replacement frequency of culture vessel 2, among culture vessels 2 in which the measured pH is below the pH threshold. That is, instructing unit 9 recognizes a discontinuous pH change of the records in recorder 4 as the operation of the replacement of the culture medium, calculates the culture medium replacement frequency, and instructs the replacement. The experiments by the inventors show that, as the culture medium replacement frequency is increased, a good deal of time has passed since the seeding process. In other words, it is found that, among culture vessels 2, culture vessel 2 in which the culture medium replacement frequency is high causes the pH to decrease at a quick pace, and there is a high probability that the pH is in a range unsuitable for cell cultivation. Accordingly, the replacement of the culture medium is performed preferentially in descending order of culture medium replacement frequency of culture vessel 2 so that it is possible to decrease the probability for the pH to be in a range unsuitable for cell cultivation. Note that, in apparatus 1 for culturing cells 1 of the exemplary embodiment, the culture medium replacement frequency of each of culture vessels 2 is 0 (reset) when cells are seeded.

Figure 5:
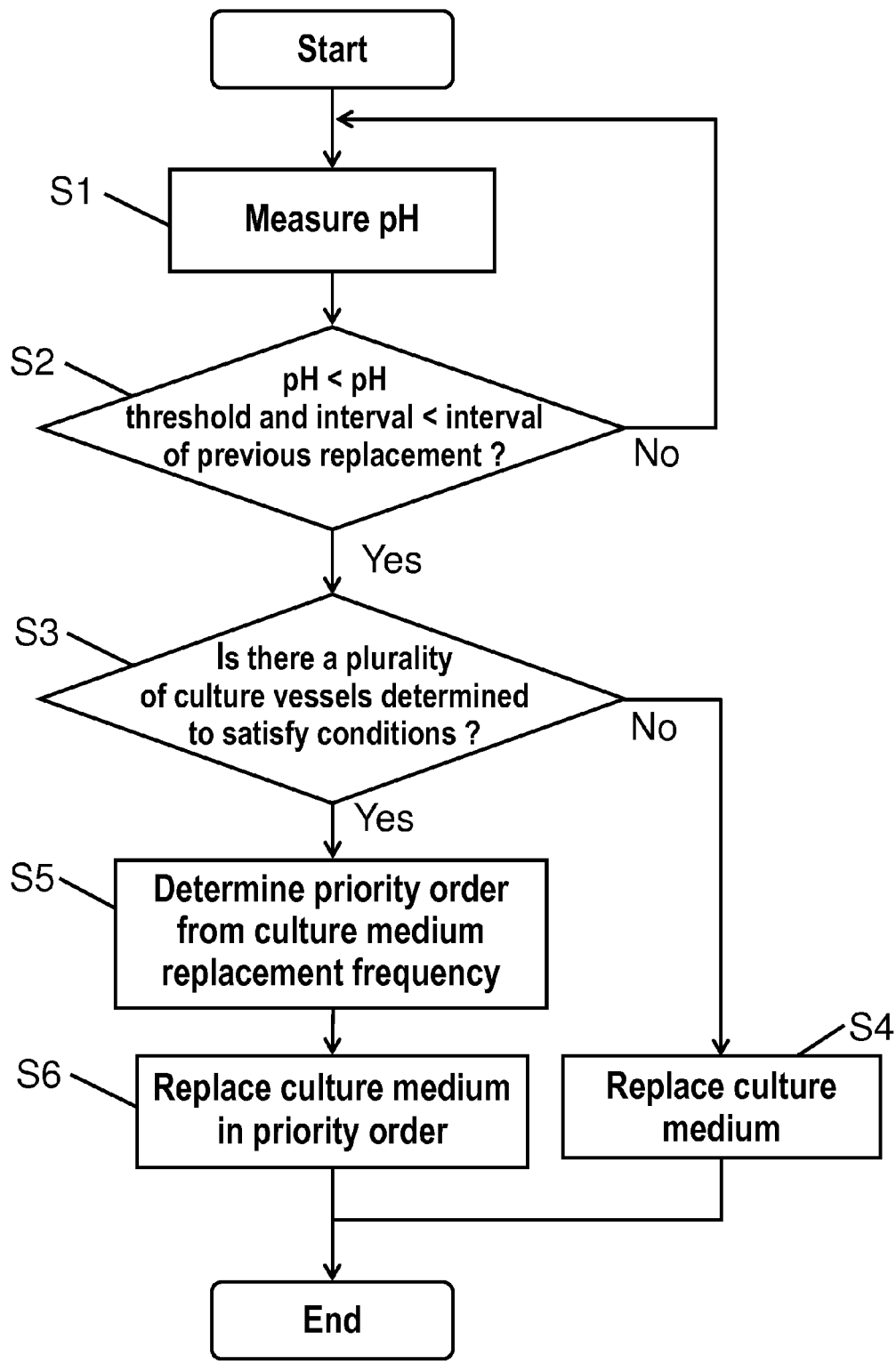
FIG. 5 is a flow chart of the replacement of the culture medium by the apparatus for culturing cells in the exemplary embodiment.
Figure 6:
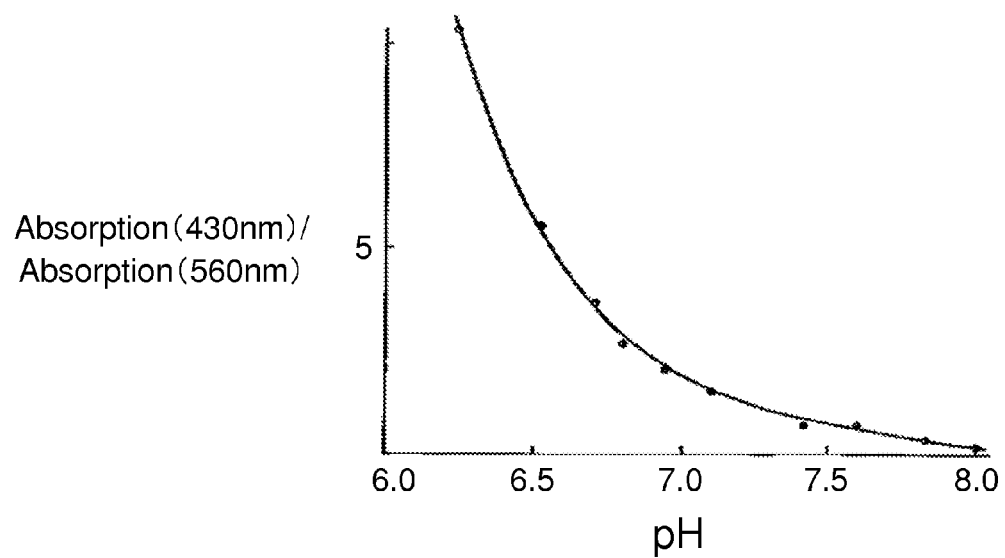
FIG. 6 is a diagram showing a relationship between absorbance and pH in a conventional apparatus for culturing cells.

The replacement of the culture medium in apparatus 1 for culturing cells of the exemplary embodiment described above will be described with reference to FIG. 5. FIG. 5 is a flow chart of the replacement of the culture medium by apparatus 1 for culturing cells in the exemplary embodiment.

As shown in FIG. 5, in Step S1, the pH of the culture medium in culture vessel 2 is first measured using measuring unit 3 and then the pH is recorded on recorder 4.

Subsequently, in Step S2, the pH of the culture medium in culture vessel 2 measured by the measuring unit 3 is compared to the pH threshold set by first setting unit 5, and it is determined whether the measured pH is less than the pH threshold. At this time, in Step S2, it is determined whether the interval is less than the interval of the previous replacement of the culture medium, namely whether the interval of the replacement of the culture medium is shorter than the interval of the previous replacement of the culture medium in the second and subsequent replacement of the culture medium. In the case where both of these conditions are satisfied in Step S2 (Yes in S2), the process proceeds to Step S3. In the case where at least one of these conditions is not satisfied (No in S2), the process returns to Step S1 and repeats the determination.

Subsequently, in Step S3, it is determined whether the number of culture vessels 2 determined to satisfy the conditions in Step S2 is plural or not. In the case where there is a plurality of culture vessels 2 determined to satisfy the conditions in Step S3 (Yes in S3), the process proceeds to Step S5. In the case where the number of culture vessels 2 determined to satisfy the conditions is one in Step S3 (No in S3), the process proceeds to Step S4.

In Step S4, the culture medium of culture vessel 2 is replaced in the case where the number of culture vessels 2 determined to satisfy the conditions is one.

In Step S5, second setting unit 8 sets the priority order to descending order of culture medium replacement frequency of culture vessel 2 in the case where there is a plurality of culture vessels 2 determined to satisfy the conditions. In Step S6, in accordance with the priority set in Step S5, the culture medium of each of culture vessels 2 is replaced in the priority order.

Note that a value obtained by passing the pH of the culture medium measured by the measuring unit 3 through a high-frequency cut-off filter such as a low pass filter may be used. The pH passed through the low pass filter is used so that the timing of the replacement of the culture medium can be accurately grasped regardless of the influences of $CO_2$ concentration. That is, in the case of using the low pass filter, a value obtained by passing the pH of the culture medium in culture vessel 2, the pH is measured by the measuring unit 3 through the low pass filter, is used as the pH measured by measuring unit 3.

This is because the pH in culture vessel 2 is dependent on $CO_2$ concentration in an incubator for storing culture vessel 2, in addition to the growth activity of the cells being cultured. The $CO_2$ concentration in the incubator is suddenly reduced due to the opening and closing of the door of the incubator. Thus, for example, the pH is passed through the low-pass filter at a cutoff frequency of 0.1 Hz so that the timing of the replacement of the culture medium can be accurately grasped regardless of the influences of $CO_2$ concentration.

Note that, in place of the low pass filter, the pH of the culture medium measured by the measuring unit 3 is calculated by differentiation to obtain a temporal subtraction, and the obtained temporal subtraction (differential value) is used to grasp the influences of $CO_2$ concentration. The pH from which the influences of $CO_2$ concentration are removed may be compared to the pH threshold. In this case, the time delay by the low pass filter can be reduced and the timing of the replacement of the culture medium can be determined sooner. In other words, in the case of differentiation, a value obtained by converting the pH of the culture medium in culture vessel 2, the pH is measured by the measuring unit 3 by a conversion formula for removing the influences of $CO_2$ concentration, is used as the pH measured by measuring unit 3.

INDUSTRIAL APPLICABILITY

The apparatus for culturing cells and the method for culturing cells of the present invention are useful in regenerative medicine and drug discovery fields.

The invention claimed is:

1. A method for culturing cells using a culture medium, the method comprising, in order to replace the culture medium in a culture vessel:
    measuring a pH of the culture medium in the culture vessel to obtain a measured pH and filtering the measured pH at a cutoff frequency of 0.1 Hz to obtain a measured pH value value;
    replacing the culture medium when the measured pH value of the culture medium in the culture vessel is less than a predetermined pH threshold at a first replacement of the culture medium; and
    replacing the culture medium when the measured pH value of the culture medium in the culture vessel is less than the predetermined pH threshold and an interval is less than an interval of a previous replacement of the culture medium at second and subsequent replacements of the culture medium,
    wherein the predetermined pH threshold is within a range of greater than or equal to 6.8 and less than or equal to 7.0.

2. A method for culturing cells using culture medium in a plurality of culture vessels, the method comprising:
    for each of the plurality of culture vessels, determining if the culture medium has a pH that is less than a predetermined pH threshold and replacing the culture medium in the respective culture vessel at a first replacement if the culture medium is determined to have the pH that is less than the predetermined pH threshold;

for each of the plurality of culture vessels, determining if the respective culture medium has a pH that is less than the predetermined pH threshold and if an interval is less than an interval of a previous replacement of the respective culture medium at second and subsequent replacements; and replacing the culture medium in each of the respective culture vessels determined to have the pH that is less than the predetermined pH threshold and the interval less than the interval of the previous replacement at the second and the subsequent replacements in descending order of a respective one of the respective culture vessels having a highest culture medium replacement frequency of each of the respective culture vessels to a respective one having a lowest culture medium replacement frequency.

3. The method for culturing cells according to claim 2, further comprising:

subtracting a differential value associated with an influence of $CO_2$ concentration from the measured pH to obtain a value to be used as the pH of the culture medium in the culture vessel.

4. A method for culturing cells using culture medium in a plurality of culture vessels, the method comprising:

for each of the plurality of culture vessels, determining if the culture medium has a pH that is less than a predetermined pH threshold and replacing the culture medium in the respective culture vessel at a first replacement if the culture medium is determined to have the pH that is less than the predetermined pH threshold;

for each of the plurality of culture vessels, determining if the respective culture medium has a pH that is less than the predetermined pH threshold and if an interval is less than an interval of a previous replacement of the respective culture medium at second and subsequent replacements;

replacing the culture medium in each of the respective culture vessels determined to have the pH that is less than the predetermined pH threshold and the interval less than the interval of the previous replacement at the second and the subsequent replacements in descending order of a respective one of the respective culture vessels having a highest culture medium replacement frequency of each of the respective culture vessels to a respective one having a lowest culture medium replacement frequency; and selecting the culture medium replacement frequency by recognizing a discontinuous pH change as an operation of the replacement of the culture medium.

* * * * *